United States Patent [19]

DeMatteis

[11] Patent Number: 5,383,477
[45] Date of Patent: Jan. 24, 1995

[54] METHOD AND APPARATUS FOR LAPAROSCOPIC REPAIR OF HERNIAS

[76] Inventor: Ralph A. DeMatteis, 1201 5th Ave. N., Ste. 400, St. Petersburg, Fla. 33705

[21] Appl. No.: 101,960

[22] Filed: Aug. 4, 1993

Related U.S. Application Data

[63] Continuation of Ser. No. 740,002, Aug. 2, 1991, abandoned.

[51] Int. Cl.⁶ .............................................. A61B 19/00
[52] U.S. Cl. .................................. 128/898; 606/151; 606/213
[58] Field of Search ............... 606/148, 151, 139, 213, 606/215, 216, 200, 127, 99, 1, 144; 600/37; 604/15, 41, 48, 288; 128/898

[56] References Cited

U.S. PATENT DOCUMENTS

| | | |
|---|---|---|
| 3,266,054 | 8/1966 | Jimenez . |
| 3,874,388 | 4/1975 | King et al. .................... 606/213 X |
| 4,007,743 | 2/1977 | Blake ............................ 606/213 X |
| 4,347,847 | 9/1982 | Usher . |
| 4,452,245 | 6/1984 | Usher . |
| 4,467,802 | 8/1984 | Maslanka .................... 606/127 X |
| 4,741,330 | 5/1988 | Hayhurst ..................... 606/232 X |
| 4,744,364 | 5/1988 | Kensey ............................. 606/213 |
| 4,769,038 | 9/1988 | Bendavid et al. ................ 623/13 |
| 4,854,316 | 8/1989 | Davis . |
| 4,865,031 | 9/1989 | O'Keefe .......................... 606/151 |
| 5,026,379 | 6/1991 | Yoon ................................ 606/141 |
| 5,041,129 | 8/1991 | Hayhurst et al. ................ 606/232 |
| 5,053,046 | 10/1991 | Janese ............................. 606/215 |
| 5,059,201 | 10/1991 | Asnis .............................. 606/144 |
| 5,108,420 | 4/1992 | Marks ............................. 606/213 |
| 5,116,357 | 5/1992 | Eberbach ........................ 606/213 |
| 5,122,155 | 6/1992 | Eberbach ........................ 606/213 |
| 5,141,515 | 8/1992 | Eberbach ........................ 606/151 |
| 5,147,371 | 9/1992 | Washington et al. ........... 606/127 |
| 5,147,374 | 9/1992 | Fernandez ...................... 606/151 |
| 5,176,692 | 1/1993 | Wilk et al. ...................... 606/151 |
| 5,192,302 | 3/1993 | Kensey et al. .................. 606/213 |

FOREIGN PATENT DOCUMENTS

| | | |
|---|---|---|
| 2822603 | 5/1978 | Germany . |
| 0554999 | 7/1943 | United Kingdom ............ 604/15 |
| 0764684 | 9/1980 | U.S.S.R. ........................... 606/1 |

OTHER PUBLICATIONS

Article entitled "Laser Laparoscopic Herniorraphy: A Clinical Trial Preliminary Results," by Leonard Schultz, M.D., et al., Journal of Laparoendoscopic Surgery, vol. 1, No. 1, 1990.

Primary Examiner—C. Fred Rosenbaum
Assistant Examiner—V. Alexander
Attorney, Agent, or Firm—Pettis & McDonald

[57] ABSTRACT

Apparatus and methods for laparoscopic repair of hernia defects are disclosed. The apparatus includes an applicator for introducing a section of surgical mesh into the abdominal cavity with that applicator having the structure and capability for spreading a section of surgical mesh within the abdomen of a patient and holding it in place for subsequent attachment over a hernia defect. The procedure involves the use of such an applicator introduced through a trochar into the abdomen of a patient that has been insufflated to establish a pneumoperitoneum, then exposing and reducing the hernia and applying the surgical mesh thereover and affixing it across the hernia defect to prevent the intra-abdominal contents of the patient from extending therethrough and then subsequently withdrawing the applicator and any such trochar and closing any openings made by those trochars through the abdomen wall.

10 Claims, 5 Drawing Sheets

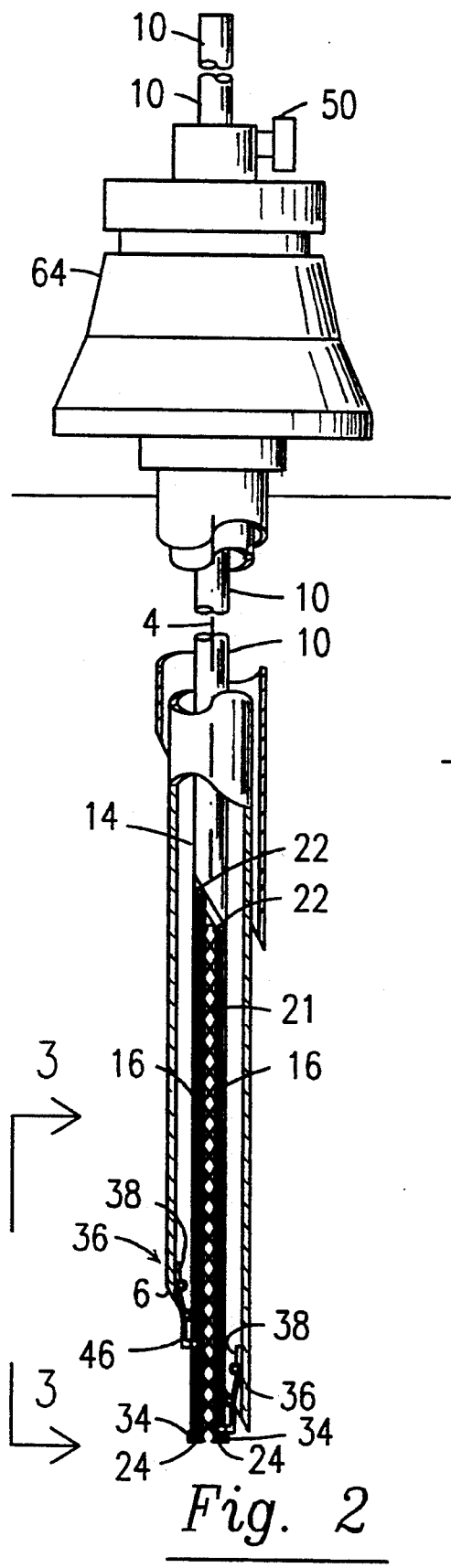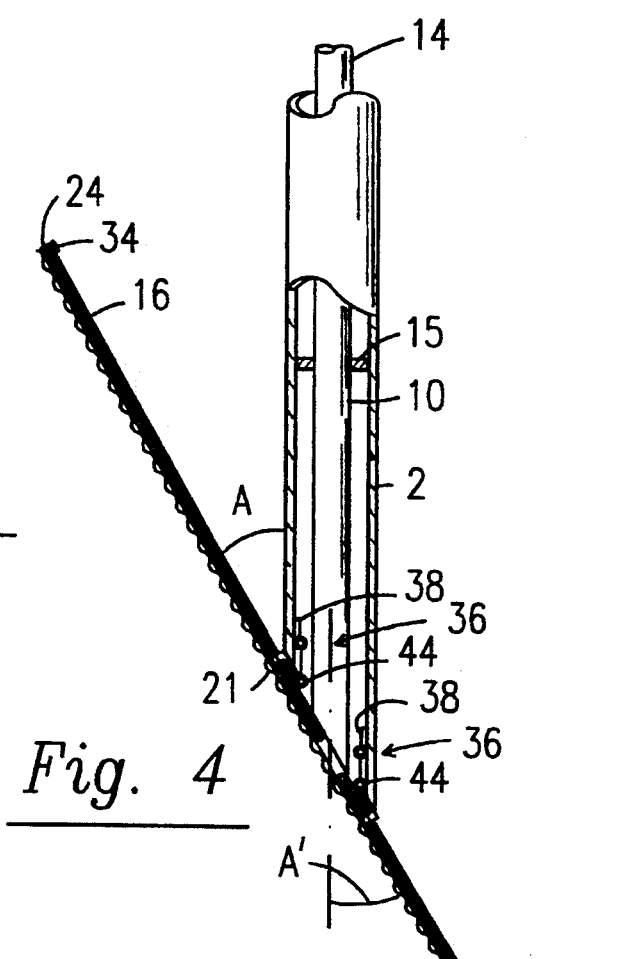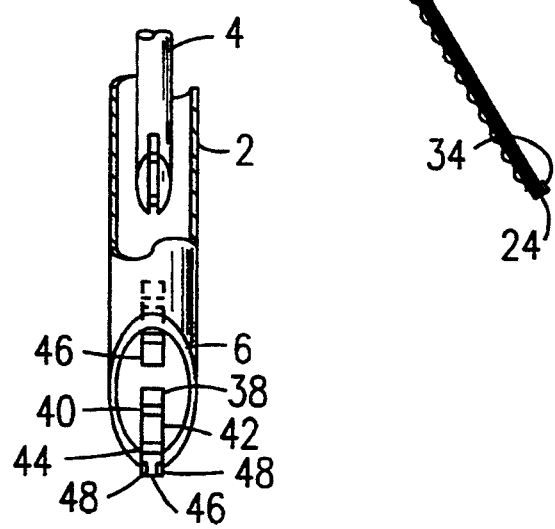

METHOD AND APPARATUS FOR LAPAROSCOPIC REPAIR OF HERNIAS

This application is a continuation of application Ser. No. 07/740,002 filed Aug. 2, 1991, and abandoned as of the filing date of the present application.

BACKGROUND OF THE INVENTION

Hernias, or ruptures, are common types of injuries, frequently caused by people attempting to lift heavy objects or otherwise straining their abdominal muscles. A hernia is a defect in the abdominal wall through which a portion of the intra-abdominal contents can protrude. This often causes discomfort and an unsightly, visible bulge in the abdomen. When such a hernia defect occurs in the abdominal region, conventional corrective surgery has required opening the abdominal cavity by surgical incision through the major abdominal muscles. While this technique provides for effective corrective surgery of the hernia defect, it has the disadvantage of requiring a hospital stay of as much as a week, during which pain is frequently intense, and it requires an extended period of recuperation. After the conventional surgery patients frequently cannot return to a full range of activity and work schedule for a month or more. Accordingly, medical science has sought alternative techniques that are less traumatic to the patient and provide for more rapid recovery.

Laparoscopy is the science of introducing a viewing instrument through a port into a patient's body, typically the abdominal cavity, to view its contents. This technique has been used for diagnostic purposes for more than 75 years. However, operative laparoscopy, in which surgical tools are inserted through a port for internal surgery is a comparatively new technique that has been in use for a decade or so. Operative laparoscopy is performed through tiny openings in the abdominal wall called ports. In most surgical techniques several ports, frequently three to six, are used. Through one port is inserted the viewing device, which conventionally comprises a fiber optic rod or bundle having a video camera affixed to the outer end to receive and display images from inside the body. The various surgical instruments are inserted through other ports to do the surgery that normally would be performed through an open incision through the abdominal wall. In laparoscopic procedures additional room for operation is generally provided by insufflation of the patient's abdomen by an inert gas, typically carbon dioxide. By the use of the laparoscope, various gynecological procedures have been performed and, more recently, gall bladder removal has been achieved through instruments inserted through additional trochars into the body. Because the laparoscopic surgical techniques require only very small holes through the abdominal wall or other portions of the body, a patient undergoing such surgery may frequently leave the hospital within one day after the surgery and resume a full range of normal activities within a few days thereafter.

Some efforts previously have been made to incorporate laparoscopic techniques into hernia repair surgery. These efforts have generally involved reducing the hernia by retracting the intra-abdominal contents away from the hernia defect and then stuffing a bundle of Mercelene surgical mesh or other suitable material into the defect to block the defect. In practicing this technique of "plugging the hole," a surgical grasper places a Mercelene patch over the plug or bundle or mesh, and that patch is clipped or stapled into place. This technique has been utilized with some success but has suffered from the requirement of stuffing a bundle of mesh into the defect and also from having no capability of spreading a patch of surgical mesh in a satisfactory manner to hold it in place smoothly and relatively rigidly during the fastening procedure. These deficiencies of this technique have caused difficulties, particularly from the inability to hold and affix such a patch in a smoothly expanded manner without causing substantial subsequent tension on the abdominal portions to which the mesh is affixed.

SUMMARY OF THE INVENTION

In order to overcome the disadvantages of prior techniques and to provide for an efficient laparoscopic repair procedure, the present invention is directed to an applicator for placing and holding a patch of surgical mesh over a hernia defect and to an advantageous laparoscopic procedure providing for an improved method of hernia repair surgery. More particularly, the invention teaches a method for repair of a hernia defect in the abdominal cavity of a patient involving insufflation of the patient to establish a pneumoperitoneum, introducing at least one trochar into the abdomen of a patient and exposing the hernia defect within the patient's abdominal cavity, reducing the sac of the hernia into the abdominal cavity, introducing a section of surgical mesh through one such trochar into the abdominal cavity to a position proximal the hernia defect and spreading that section of surgical mesh adjacent the preperitoneum of the patient and across the transversalis fascia with its hernia defect and holding it in that position and then affixing that section of surgical mesh to the transversalis portion of the abdominal wall of the patient to prevent the abdominal contents of the patient from extending therethrough and then withdrawing all such trochars and closing any openings made by passage of the trochars through the abdomen. The invention further is directed to a hernia repair mesh applicator for introducing a section of surgical mesh into the abdominal cavity of a hernia patient and positioning that mesh over a hernia defect in the abdominal wall. Such an applicator includes an outer cylinder having opposed first and second axial ends and having a predefined central axis, with that outer cylinder being insertable through a trochar extending into the abdomen of the patient, and further includes an inner member mounted for movement within the outer cylinder, generally parallel to the central axis, and apparatus for selectively moving that element between first and second positions. The inner member includes opposed first and second axial ends and has at least one element attached proximal the first end thereof and being selectively movable between such a first position extending generally parallel to the central axis and a second position extending at an acute angle to the central axis. This element has a section of surgical repair mesh releasably attached thereto, such that movement of the element to that second position extends at least a portion of the surgical repair mesh generally transverse to the central axis, whereby the surgical repair mesh may be spread over a hernia defect to be repaired.

BRIEF DESCRIPTION OF THE DRAWINGS

A preferred embodiment of the present invention will be described in detail below in connection with the drawings in which:

FIG. 2 is a side sectional view of the hernia repair apparatus of FIG. 1 inserted through a trochar into a bodily cavity, with the repair apparatus in its retracted position;

FIG. 3 is a side elevational view, partially in section, taken along lines 3—3 of FIG. 2;

FIG. 4 is a side sectional view of the inner end of the apparatus of FIG. 1, with the mesh supporting elements shown in their extended position;

DESCRIPTION OF PREFERRED EMBODIMENTS

Preferred embodiments of both the apparatus and the procedure of the present invention will be described below in connection with the various drawings.

Figure 1:
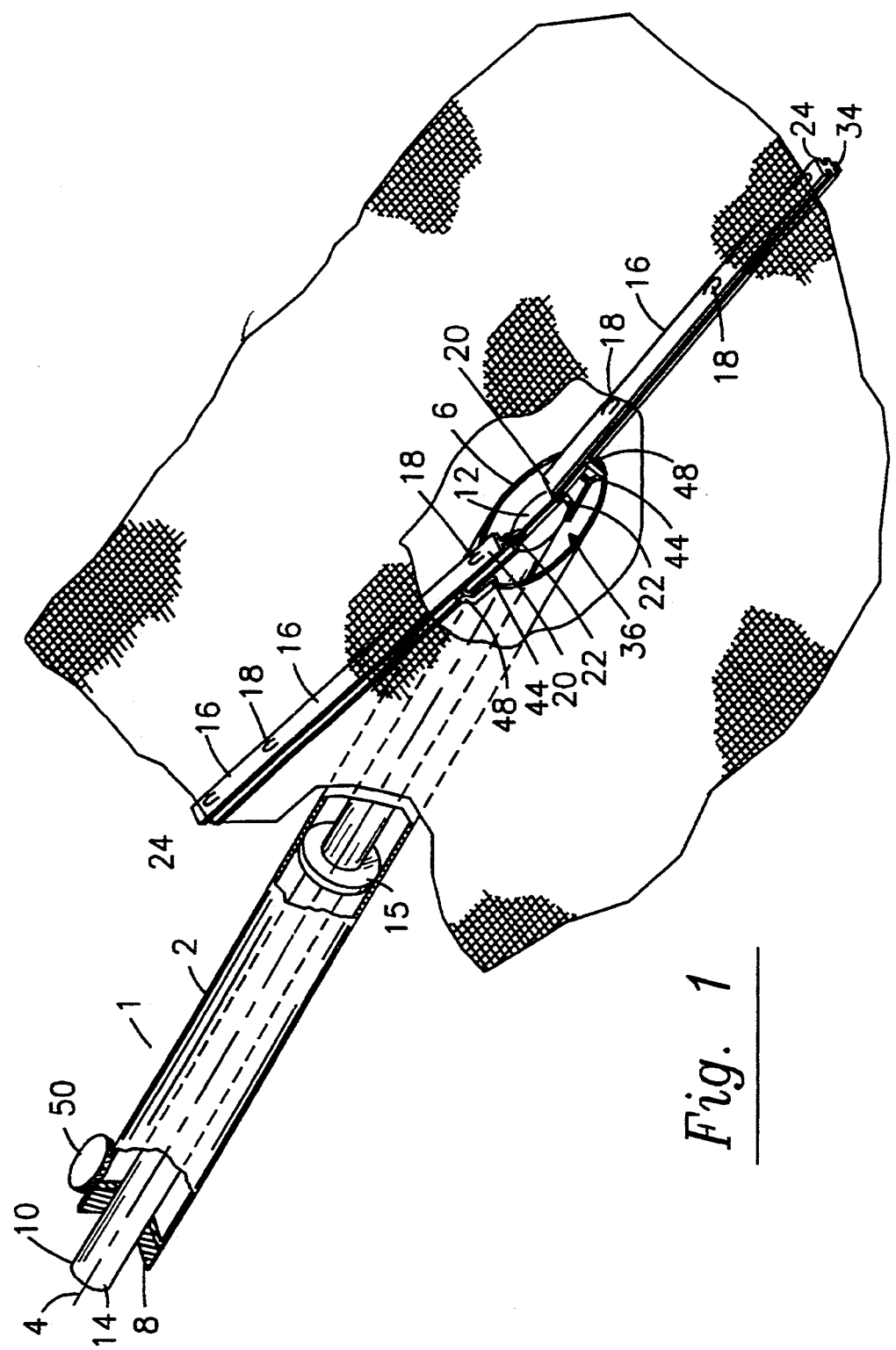
FIG. 1 is a perspective view, partially in section, of the hernia repair apparatus of the present invention in its extended configuration.
Figures 5A, 5B:
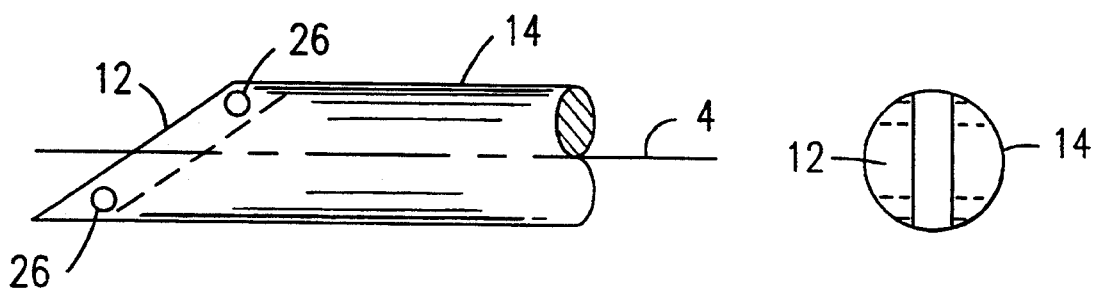
FIGS. 5a and 5b are, respectively, fragmentary side and inner end views, at substantially larger scale, of the actuator rod of the apparatus of FIG. 1.

FIG. 1 illustrates a preferred embodiment of the hernia repair mesh applicator 1 of the present invention in its extended configuration with a section of repair mesh spread open for application across a hernia defect. This applicator 1, which may suitably be fabricated of a rigid material, such as stainless steel, includes an outer cylinder 2 having a predefined cylindrical axis 4 and a first axial end 6, as well as an opposed, second axial end 8. This outer cylinder 2 is dimensioned to be insertably receivable through a known surgical port or trochar for insertion into a bodily cavity, such as the abdomen of a patient.

Mounted within that outer cylinder 2 is an inner member 10 extending generally coaxially with cylinder 2 and having a first axial end 12 and an opposed, second axial end 14. This inner member 10 is mounted for movement within said outer cylinder 2 generally parallel to said central axis 4 and supported for such movement by guide element 15. Proximal the first end 12 of said inner member 10 is attached at least one element 16, and preferably a plurality of such elements 16. On each of these elements 16 are provided means, such as hooks 18, for releasably attaching a section of surgical mesh 21, such as that commonly sold under the trademark MERCELENE. Each of the elements 16 includes an outer end 24 and an opposed inner end 20 pivotally joined to the inner member 14 by pivotal connections, conveniently in the form of a journal 22 through which is received a suitable shaft or pin 26 which is also received through the inner member 14 in a direction generally transverse to the axis 4 thereof.

Figure 6:
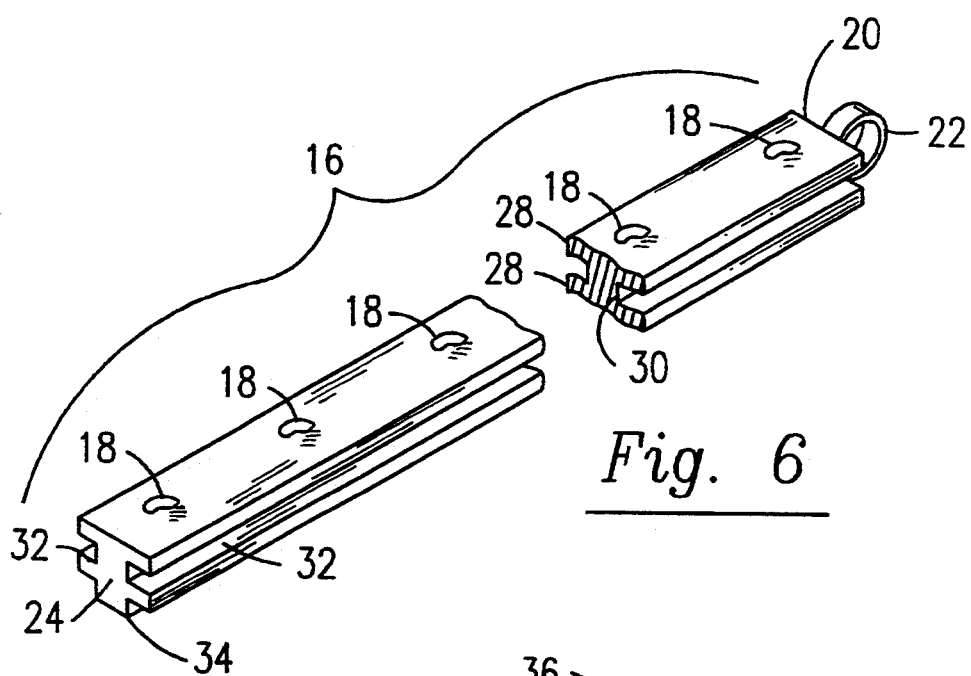
FIG. 6 is a fragmentary perspective view, at substantially larger scale, of a mesh carrying rib of the apparatus of FIG. 1.

A preferred embodiment of the element 16 is illustrated more clearly on an enlarged scale in FIG. 6. In FIG. 6 one such element 16 is shown, broken for purposes of more compact illustration, and having a generally I-shaped cross section formed of a pair of spaced, parallel flanges 28 joined by a central web 30. This configuration thus defines a pair of slots 32 extending longitudinally of the element 16. A tab 34 extends generally radially outwardly of the outer end 24 of the element 16 for purposes to be described below.

Figure 7:
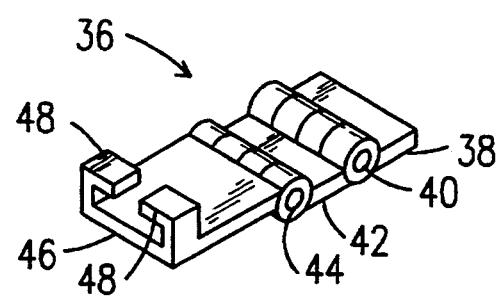
FIG. 7 is a perspective view, again at larger scale, of one of the pivoting members affixed to the inner end of the hernia repair apparatus of the present invention for slidably and hingeably supporting the ribs of FIG. 6.

More clearly illustrated in FIGS. 2–4, are pivoting members 36 having one portion thereof affixed to the outer cylinder 2 for engaging the elements 16 for reasons to be described below. A preferred embodiment of the pivoting member 36 is illustrated more clearly in the enlarged view of FIG. 7. This pivoting member 36 includes a first portion 38 attachable to the radially inner portion of the outer cylinder 2 at a location proximal the first end 6 thereof, connected through a pivotal connection 40 to an intermediate member 42 and then through a second pivotal connection 44 to a guide portion 46. In this embodiment the guide portion 46 includes a pair of fingers or elements 48 extending toward one another to provide a generally C-shaped structure, with those fingers 48 being receivable into the longitudinally extending grooves 32 of the elements 16.

The functioning of these pivoting members 36 is best illustrated in FIGS. 1–4. FIG. 2 illustrates the apparatus in which the elements 16 are in their first position and preferably within the outer cylinder 2, with each element 16 extending generally parallel to the central axis 4 and with the surgical mesh material 21 furled closely adjacent those members 16. The outer portions 24 of the members 16 are received by the pivoting members 36 with the fingers 48 thereof slidably engaging the longitudinal grooves 32 of the member 16, with those members 16 being slidable within the grasp of the fingers 48 of the pivoting members 36. As best shown in FIG. 2, the tabs 34 limit the sliding of the elements 26 longitudinally inwardly of the pivoting members 36.

The inner member 10 of the apparatus of this invention is slidable longitudinally of the axis 4 generally between a first position illustrated in FIG. 2 and a second position illustrated in FIGS. 1 and 4. In the first position of FIG. 2 the elements 16 are substantially retracted within the outer cylinder 2, extending generally parallel to the central axis 4. By advancing the inner member 10 longitudinally outwardly of the first end 6 of outer cylinder 2, the members 16 are first extended axially outwardly of the outer cylinder 2. Then, as the first end 12 of the inner member 10 approaches the first end 6 of the outer cylinder 2, the pivotal connection of the elements 16 to that inner member 10 and the reception of those elements within the fingers 48 of the pivoting elements 36 then urge the elements 16 to pivot about connection 44 to the extended position shown in FIGS. 1 and 4. In this position the elements 16 then extend at angles A and A' with respect to the central axis, generally as illustrated in FIGS. 1 and 4. In this preferred embodiment the angles A and A' are preferably in the range of about 30 degrees to 60 degrees.

As shown in FIG. 1, the unfolding of the elements 16 effects an unfurling and stretching open of the section of surgical repair mesh 21. Suitable means such as a thumb screw 50, or the like, extending through the outer cylinder 2, provides for releasably holding the inner member 10 in any predetermined position of its movement, either opened or closed. As shown on FIG. 1, the releasable attaching means, such as hooks 18, carry the section of surgical mesh 21 on the elements 16 for subsequent release, in a manner to be described below.

The hernia repair applicator of this invention having been described above, one preferred method of hernia repair will be described below, utilizing such applicator. In this procedure the abdomen of the patient is first insufflated with an inert gas, conveniently carbon dioxide, by a veress needle inserted through the umbilicus. A first trochar is then inserted, through which is introduced a light source to transluminate the hernia sac to locate the thinnest avascular entry point for additional trochars or laparoscopic entry ports. Two additional trochars are introduced into the abdomen, one about 6–10 cm laterally of the first trochar, on the side where the hernia is located, and the second about 6–10 cm laterally toward the opposite side of the patient. The first additional trochar, closest to the hernia, is preferably of about 10–12 mm diameter, with the second trochar, distal the hernia, suitably being on the order of about 5 mm, with all of the trochars or ports being of conventional configuration.

Figure 8:
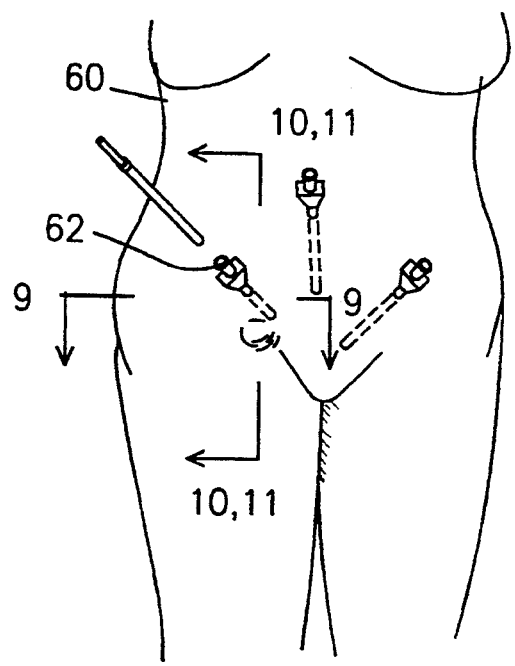
FIG. 8 is a representation of a human body depicting preliminary steps in the repair of a hernia using the method of the present invention.
Figure 9:
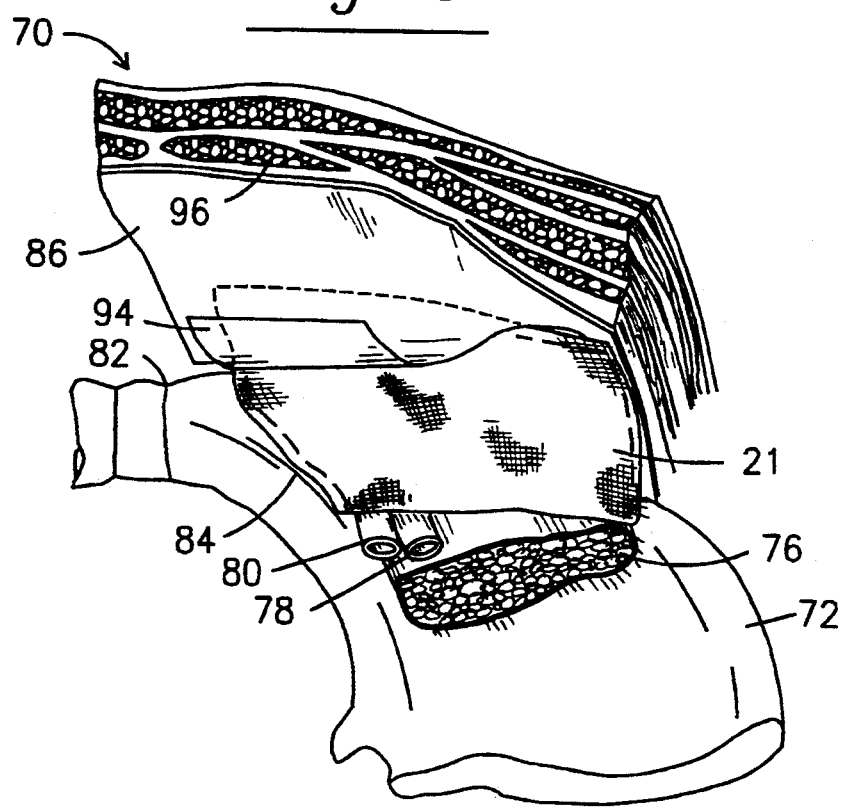
FIG. 9 is a sectional view taken along lines 9—9 of FIG. 8 illustrating a portion of the right side of the pubic region of the patient of FIG. 8, from the inside looking out.

With the trochars in place and the pneumoperitoneum established, the surgeon can view the interior of the insufflated abdomen through conventional laparoscopic optical or video viewing equipment inserted through one of the trochars. This arrangement of trochars is generally illustrated in FIG. 8. On the representation of the patient's body 60 in FIG. 8 are shown section lines through the body indicating the various views illustrated in FIGS. 9 through 11. FIG. 9 depicts an interior view of a portion of the patient's abdomen, looking down into the front of the patient, while FIGS. 10 and 11 depict side sectional views of the patient's abdomen, looking from the inside out, toward the right side of the patient.

Figure 10:
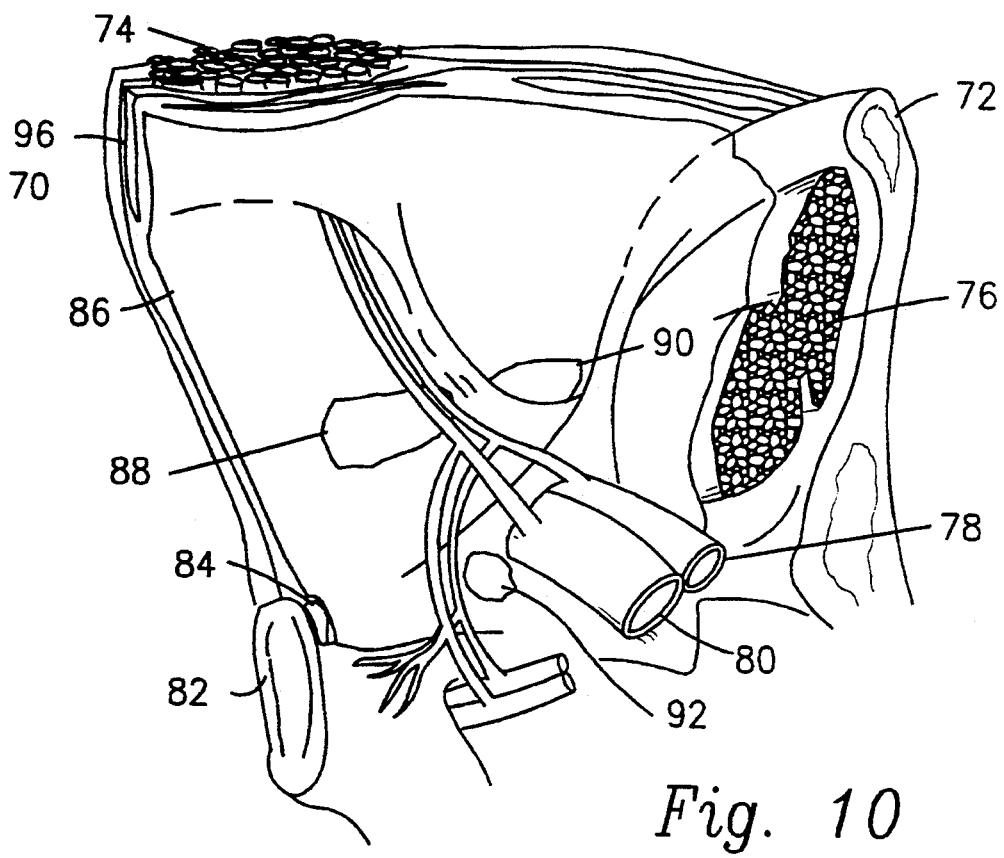
FIG. 10 is a sectional view of a portion of the interior pubic region of the patient of FIG. 8 taken along lines 10—10 of FIG. 8, illustrating possible positions of various hernias.
Figure 11:
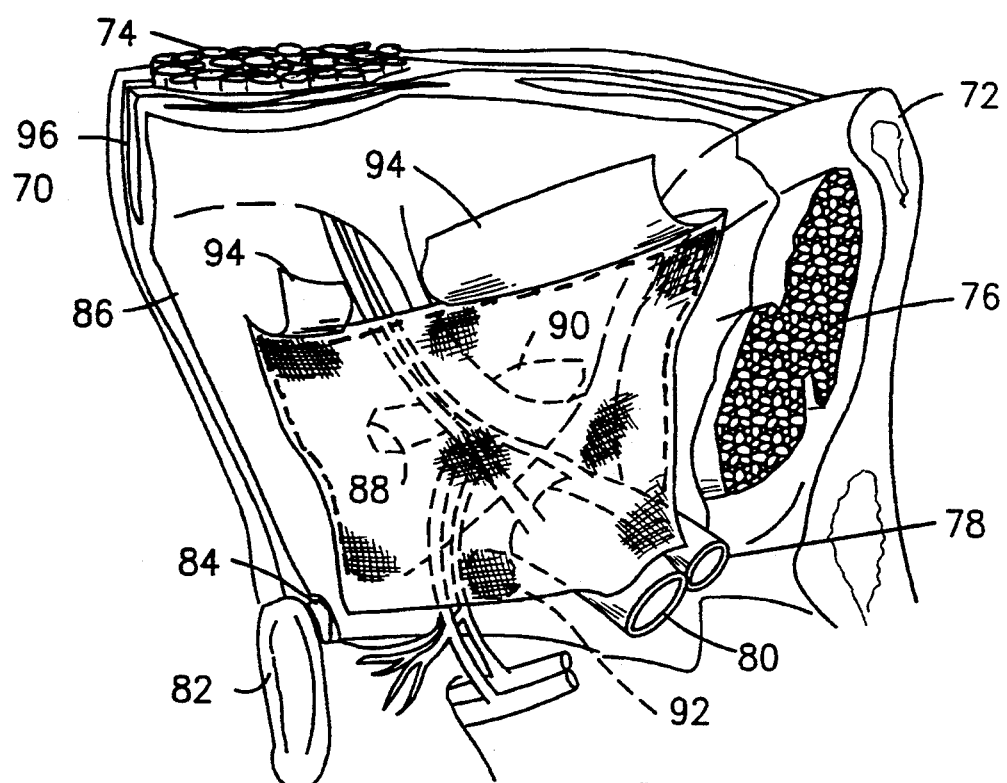
FIG. 11 is a sectional view similar to that of FIG. 10 but illustrating the placement of a surgical mesh repair according to the procedures of this invention.

FIG. 10, an internal side sectional view of the right side of the patient's abdomen, illustrates the position of three common types of hernias. In this view reference numeral 70 depicts the anterior portion of the patient, with reference numeral 72 depicting the posterior portion. Two the major muscles, the rectus muscle 74 and the psoas muscle 76 are also illustrated, along with the femoral artery 78, the femoral vein 80 and the pubic bone 82, which comprises a portion of the pelvis. Adjacent the pelvis 82 may also be seen Cooper's ligament 84, covered by the peritoneum 86, through which peritoneum the hernia defects represent voids or lesions. For purposes of illustration FIG. 10 depicts the position of a direct inguinal hernia 88, an indirect hernia 90 and the femoral hernia 92, although the occurrence of all three such hernias in a single patient would be unusual.

The sac of the hernia, which for the purposes of this description may be the indirect hernia 90, is first reduced back into the abdominal cavity as an initial step in this laparoscopic procedure, so that there remains simply the hernia defect in the peritoneum 86 and the transversalis muscle 96. Preferably, but not necessarily, the portions of the peritoneum 86 adjacent the hernia defect are dissected and laid back from the hernia defect as flaps 94 to expose the defect for repair. At this point a section of surgical mesh 21 is then introduced through one of the trochars 62–66, while attached to the applicator 1, generally as illustrated in FIG. 2. The applicator 1 is in its closed configuration, as depicted in FIG. 2 and is inserted through the appropriate trochar or port, which may suitably be port 64. At this point the surgical mesh 21 is folded within the elements 16 and remains within the outer cylinder 2 for insertion into the patient's abdomen. The inner member 10 may then be advanced longitudinally of the outer cylinder 2, inwardly of the patient in the manner illustrated in FIGS. 1 and 4. The advancement of inner member 10 longitudinally of the hernia repair mesh applicator serves to open the elements 16 to their extended position, depicted in FIGS. 1 and 4. This action serves to unfurl and spread the surgical mesh 21 as it extends the elements 16. The mesh 21 is then held against the transversalis muscle 96 in the preperitoneal plane and positioned over the hernia defect 90 under laparoscopic view and control. The elements 16 of the mesh applicator 1 serve to hold the mesh 21 in place. With it held in place, the mesh 21 is then stapled or otherwise affixed to a portion of the abdominal wall, suitably the transversalis fascia 96, by means of a stapler inserted through one of the other trochars.

Once a portion of the mesh 21 has been stapled in place, suitably the portion adjacent the elements 16, the inner member 14 of the applicator 1 may be withdrawn slightly, to effect a slight collapsing of the elements 16. This will enable the mesh 21 to slip free of the retaining hooks 18 on the elements 16. At this point the applicator 1 may be moved slightly to urge another portion of the mesh 21 snugly against a portion of the wall, such as the transversalis fascia 96, whereupon that portion may be stapled in place, with this procedure being repeated until the entire section of mesh has been stapled in place. When the mesh 21 has been affixed all around its periphery, the flaps 94 of the peritoneum may then be urged back in place over the mesh and affixed by suitable means such as staples or sutures. At this point the applicator 1 may be withdrawn from the trochar and the abdomen of the patient irrigated in the conventional manner. The surgical ports or trochars are then removed and the small incisions for those trochars are closed in the usual manner, such as by a small suture.

It is to be understood that numerous variations on this technique will readily occur and may be required in various different situations. For example, instead of cutting and opening the flaps 94 of the peritoneum 86 to apply the mesh directly to the transversalis fascia 96, it is also possible to apply the mesh directly to the peritoneal plane, overlying the peritoneum. It is also to be understood that various steps may be necessary in reducing the hernia. For example, if the hernia sac, particularly an indirect type hernia, cannot readily be reduced into the abdominal cavity, the peritoneal plane approach noted above may be used. If the hernia is prolapsed into the abdominal cavity, then use of the known push-pull technique may serve to define the peritoneal plane, with the mesh then being applied in that plane. Also, if need be, when the hernia sac is opened laparoscopically and the mesh graft stapled against the transversalis fascia, the excess peritoneum or hernia sac may, if desired, be amputated, with the surgical mesh fastened in place and exposed within the abdomen. Also, the applicator may be configured with 1, 2, 3, 4 or any other desired number of mesh supporting elements 16. It is to be recognized that these alternatives represent but a few of the numerous variations and modifications of both the apparatus and the method of this invention and that numerous other such variations, all within the scope of the invention, will readily occur to those skilled in the art. Accordingly, the foregoing is to be considered as illustrative only of the principles of the invention and is not to be considered limitative thereof. The scope of the invention is to be defined solely by the claims set forth below.

What is claimed is:

1. A hernia repair mesh applicator for introducing a section of surgical mesh into the abdominal cavity of a hernia patient and positioning such mesh over a hernia defect in the abdominal wall, such applicator comprising:
    an outer cylinder having opposed first and second axial ends and having a predefined central axis, said outer cylinder being insertable through a trochar extending into the abdomen of the patient;
    an inner member mounted for movement within said outer cylinder generally parallel to said central axis, said inner member including opposed first and second axial ends;
    at least one element attached proximal said first end of said inner member, wherein said element is movable between a first position extending generally parallel to said central axis, and a second position extending at an angle to said central axis;
    a surgical repair mesh releasably attached to said element;
    a releasable attaching means attaching said surgical repair mesh to said element; and
    means for selectively moving said element between said first position and said second position;
    wherein movement of said element to said second position extends at least a portion of said surgical repair mesh in a generally planar manner, and wherein said releasable attaching means releases said mesh from said element, without destruction of said element, upon movement of said element to said second position, by a user of said applicator, and wherein said surgical repair mesh is spread over a hernia defect to be repaired.

2. The applicator of claim 1 further comprising at least two said elements selectively movable between said first position with each extending generally parallel to said central axis and said second position in which both said elements extend outwardly from said central axis, whereby the surgical repair mesh may be spread by both such elements.

3. The applicator of claim 1 wherein said surgical repair mesh is releasably attached to said element by releasable attaching means.

4. The applicator of claim 3 wherein said releasable attaching means comprises resilient hooks.

5. The applicator of claim 1 further comprising means for releasably holding said inner member in a predetermined axial position relative to said outer cylinder.

6. The applicator of claim 1 wherein said acute angle comprises an angle in the range of about 30 degrees to 60 degrees.

7. The applicator of claim 1 further comprising means attached to said outer cylinder for engaging said element and urging said element toward said second position during movement of said inner member generally axially of said outer cylinder and inwardly of said patient abdominal cavity.

8. The applicator of claim 7 wherein said urging means comprises a pivoting member for providing pivoting movement of said element during at least a portion of said axial movement of said element relative to said outer cylinder.

9. The applicator of claim 8 wherein said element comprises a member having an I-shaped cross section formed of a pair of spaced, parallel flanges joined by a central web.

10. The applicator of claim 9 wherein said pivoting member includes guide portions slidably receiving therewithin one of said element flanges to provide for slidable movement of said received flange relative to said pivoting member.

* * * * *